United States Patent [19]

Rainer

[11] 4,042,702
[45] Aug. 16, 1977

[54] HALOGEN PYRAZOLE DERIVATIVES, A METHOD FOR PRODUCING THESE HALOGEN PYRAZOLE DERIVATIVES, MEDICAMENTS CONTAINING AND METHODS OF USING THEM

[75] Inventor: Georg Rainer, Constance, Germany

[73] Assignee: Byk Gulden Lomberg Chemische Fabrik GmbH, Germany

[21] Appl. No.: 627,707

[22] Filed: Oct. 31, 1975

Related U.S. Application Data

[63] Continuation of Ser. No. 497,380, Aug. 14, 1974, abandoned.

[30] Foreign Application Priority Data

Aug. 16, 1973 Luxembourg .................... 68238

[51] Int. Cl.$^2$ ................ A61K 31/415; A61K 31/535; C07D 231/10

[52] U.S. Cl. .................... 424/273 P; 424/248.54; 548/377; 548/374; 544/140

[58] Field of Search .................... 260/310 R, 247.2 R; 424/273, 248

[56] References Cited

FOREIGN PATENT DOCUMENTS 755,924 0000 Belgium
2,438,779 2/1975 Germany

OTHER PUBLICATIONS

Burger, "Medicinal Chemistry", Third Ed. Part I, Wiley-Intersciecne, publisher (1971), pp. 64, 71 & 72.
Chemical Abstracts, vol. 83:28221k (1975).

Primary Examiner—Donald B. Moyer
Attorney, Agent, or Firm—Berman, Aisenberg & Platt

[57] ABSTRACT 1,3-Diaryl-5-halogen-pyrazole-4-acetic acids and their derivatives with analgetic, antipyretic and antiphlogistic action are described.

18 Claims, No Drawings

HALOGEN PYRAZOLE DERIVATIVES, A METHOD FOR PRODUCING THESE HALOGEN PYRAZOLE DERIVATIVES, MEDICAMENTS CONTAINING AND METHODS OF USING THEM

This application is a continuation of copending, but now abandoned, application Ser. No. 497,380, filed Aug. 14th, 1974.

The invention relates to pharmaceutically valuable halogen pyrazole derivatives, a method for producing them and medicaments which contain these active substances.

The Belgian patent specification No. 755,924 describes pyrazole-4-acetic acid derivatives of the general formula

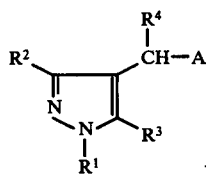

in which $R^1$, $R^2$ and $R^3$ can be the same or different and denote respectively a hydrogen atom, a straight chained or branch chained saturated or unsaturated aliphatic or cycloaliphatic hydrocarbon radical with 1 to 7 carbon atoms or a possibly substituted aryl or heteroaryl group with up to 12 carbon atoms, with the proviso that when $R^2$ is hydrogen, $R^3$ is neither hydrogen nor a methyl group, and $R^1$ additionally denotes a benzyl group, which can be substituted with a halogen atom or an alkoxy group with 1 to 4 carbon atoms, $R^4$ denotes a hydrogen atom or an alkyl group with 1 to 3 carbon atoms or a cycloalkyl group with 3 to 6 carbon atoms, A denotes COOH, $COOR^5$, $CONR^6R^7$, CN or $C(=NOH)OH$, whereas $R^5$ denotes an alkyl group with 1 to 4 carbon atoms, a benzyl group, a phenyl group or a 2-carboxyphenyl group, and $R^6$ and $R^7$ denote respectively a hydrogen atom and/or an alkyl group with 1 to 4 carbon atoms or together with a nitrogen atom form a pyrrolidino, piperidino or morpholino group.

The described group of compounds possesses antiphlogistic, analgesic and antipyretic properties.

A new class of pyrazole acetic acid derivatives has now been discovered which is characterised by a novel quite specific type of substitution which is not mentioned in the patent specification or rendered obvious by it, and in which a halogen atom is tied directly with the pyrazole nucleus. It has further been discovered that the representatives of this class have particularly advantageous pharmacological effects. In particular the invention is based upon the knowledge that pyrazole-4-acetic acids with a halogen substitution in the 5-position of the pyrazole nucleus are characterised by distinctive and specific pharmacological effects. The compounds of the invention in particular exhibit antiinflammatory, but also antipyretic and analgesic effects.

One form of subject matter of the present invention is therefore represented by pyrazole-4-acetic acid derivatives of the following general formula I -continued

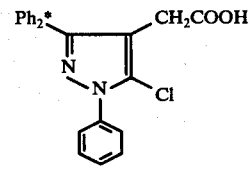

in which $Ph_1$ and $Ph_2$ are the same or different phenyl radicals, and halogen denotes a halogen atom selected from the group consisting of fluorine, chlorine or bromine, and their salts with inorganic or organic bases.

Preferred pyrazole-4-acetic acid derivatives of the general formula I and their salts with inorganic or organic bases are characterised in that $Ph_1$ denotes an unsubstituted phenyl radical and $Ph_2$ denotes a phenyl radical selected from the group comprising unsubstituted phenyl, halogenphenyl, p-lower alkoxy phenyl and p-lower alkyl phenyl, and halogen denotes a bromine or chlorine atom. By the expressions, "lower alkoxy" and "lower alkyl", radicals with a carbon atom number of 1 to 4 are understood.

Another group of preferred pyrazole-4-acetic acid derivatives of the general formula I and their salts with inorganic or organic bases is characterised in that $Ph_1$ denotes an unsubstituted phenyl radical and, $Ph_2$, a phenyl radical selected from the group consisting of unsubstituted phenyl, p-chlorophenyl and p-bromophenyl, and halogen denotes a fluorine or chlorine atom.

Especially valuable pharmacological properties are possessed by the compounds of the general formula I*

I* wherein $Ph_2^*$ denotes an unsubstituted phenyl radical or a p-chlorophenyl radical, as well as their salts with inorganic or organic bases.

A group of compounds, which to a particularly preferred extent has the distinctive pharmacological properties of the pyrazole acetic acid derivatives of general formula I and their salts, is characterised in that $Ph_1$ denotes an unsubstituted phenyl radical and $Ph_2$ denotes an unsubstituted phenyl, a p-chlorophenyl, a p-methoxyphenyl or a p-isobutylphenyl radical and halogen denotes a chlorine or bromine atom.

The following compounds, in the form of the free acid or its salts, which are distinguished with respect to their pharmacological properties, are new mentioned primarily:

5-chloro-1,3-diphenyl-pyrazole-4-acetic acid
5-chloro-3-p-chlorophenyl-1-phenyl-pyrazole-4-acetic acid
5-chloro-3-m-chlorophenyl-1-phenyl-pyrazole-4-acetic acid
5-chloro-3-p-methoxyphenyl-1-phenyl-pyrazole-4-acetic acid
5-chloro-1-phenyl-3-p-tolyl-pyrazole-4-acetic acid
5-chloro-3-p-isobutylphenyl-1-phenyl-pyrazole-4-acetic acid
5-bromo-1,3-diphenyl-pyrazole-4-acetic acid.

I,

As further typical representatives within the scope of the invention the following acids and their salts are to be considered:

5-chloro-3-p-fluorophenyl-1-phenyl-pyrazole-4-acetic acid
3-p-bromophenyl-5-chloro-1-phenyl-pyrazole-4-acetic acid
5-bromo-3-p-fluorophenyl-1-phenyl-pyrazole-4-acetic acid
5-bromo-3-p-chlorophenyl-1-phenyl-pyrazole-4-acetic acid
5-bromo-3-p-methoxyphenyl-1-phenyl-pyrazole-4-acetic acid
5-bromo-3-p-isobutylphenyl-1-phenyl-pyrazole-4-acetic acid
5-fluoro-1,3-diphenyl-pyrazole-4-acetic acid
3-p-chlorophenyl-5-fluoro-1-phenyl-pyrazole-4-acetic acid
5-fluoro-3-p-methoxyphenyl-1-phenyl-pyrazole-4-acetic acid
5-chloro-3-p-butoxyphenyl-1-phenyl-pyrazole-4-acetic acid.

Among the salts in accordance with the invention the pharmacologically-compatible salts are preferred. As cations for salt formation more particularly the cations in the form of alkali metal, alkaline earth metal and earth metal ions are used, or the ammonium ion, but also the corresponding cation acids of single or polybasic organic nitrogen bases, especially organic amines come into question.

For example use is made of the cations of the metals lithium, sodium, potassium, magnesium, calcium and aluminium and the cation acids of ethanolamine, diethanolamine, triethanolamine, ethylenediamine, dimethylamine, diethylamine, morpholine, piperazine, methylcyclohexylamine, glucosamine, N-methylglucamine, N-methylglucosamine, and furthermore of tert.-butylamine, dibutylamine, diisopropylamine, triethylamine, isopropylamine and quinoline.

A further form of subject matter of the invention is constituted by a method for the production of compounds of the general formulae I and I* and their salts with inorganic or organic bases. This method starts from functional carboxylic acid derivatives of pyrazole-4-acetic acids of the general formula I, which are described by the general formula II

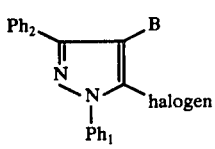

II, in which $Ph_1$, $Ph_2$ and halogen have the above-given meanings and B denotes a functional derivative of an acetic acid group.

A functional derivative of an acetic acid group is a derivative of the acetic acid group (—CH₂COOH) which derivative stands in a close chemical relation to the acetic acid group and which can be converted to the free acetic acid group by hydrolysis. Typical representatives of functional derivatives of the acetic acid group are disclosed in the following description.

The method for the production of compounds of general formulae I and I* is characterised in that compounds of the general formula II are hydrolysed to form compounds of the general formulae I and I* or their salts and, if required, the compounds obtained of the general formulae I and I* are converted into their salts or, if desired, a compound, obtained in the form of a salt, of the general formulae I and I* is converted into the free acid.

In a preferred embodiment of the hydrolysis functional pyrazole-4-acetic acid derivatives of the general formula II' are taken as a basis, that is to say

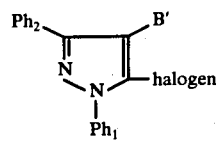

II' in which $Ph_1$, $Ph_2$ and halogen have the above-given meanings, B' denotes the group —CH₂CN or the group

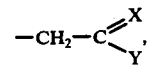

X denotes an oxygen or a sulfur atom or a substituted nitrogen atom, more particularly an imino, alkylimino or hydroxymimino group, and Y denotes a hydroxyl group or a monovalent eliminatable electrophilic radical, more particularly a free or substituted amino group, preferably a monoalkyl or dialkyl or aryl amino group, a hydroxyamino or hydrazino group, a hydrazobenzene group, a 2-hydroxyethylamino group, a free or substituted mercapto group, preferably an alkylthio group, a substituted hydroxy group, preferably an alkoxy group, an azido, a chlorine or bromine radical, a morpholino or a piperidino group, whereas Y is not a hydroxy group when X denotes an oxygen atom.

The term alkyl radica of an alkylimino, of a monoalkylamino, of a dialkylamino, of an alkylthio and an alkoxy group is understood to mean an alkyl radical with up to 6 carbon atoms and the term aryl radical of an arylamino group is taken to mean an aryl radical with up to 1 carbon atoms.

In a further preferred embodiment of the hydrolysis functional pyrazole-4-acetic acid derivatives of the general formula II' are taken as a starting material, in which B' denotes the group —CH₂CN or the group

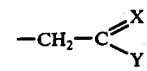

in which
X denotes an oxygen atom, a sulfur atom or an imino group and
Y denotes an amino, monoalkylamino, dialkylamino, phenylamino, alkoxy, alkylthio, chlorine or bromine radical.

In accordance with a particularly preferred embodiment of the hydrolysis pyrazole-4-acetonitriles, pyrazole-4-acetic amines and pyrazole-4-acetic acid alkyl esters of the general formula II' are taken as a starting material.

The method can also be carried out in such a manner that a pyrazole derivative is used which as an intermediate forms a pyrazole derivative of the general formulae II or II', which is reacted later with a water providing medium to produce the desired pyrazole-4-acetic acid derivative of the general formula I. In many cases the hydrolysis is carried out in a number of stages and if the reaction is carried out suitably, intermediate stages can also be isolated. Thus for example the hydrolysis of the nitriles, thioamides, amidines and imidazolines is via the corresponding amides or that of the imide acid esters is via carboxylic acid esters. In the case of the reaction of unsubstituted amides with nitric acyldiazonium compounds are produced as intermediates which can readily be hydrolysed to form carboxylic acids.

As starting compounds for the method in accordance with the invention for the production of compounds of the general formula I use is made in principle of such compounds, as functional derivatives of the carboxylic acids of general formula I produce the compounds of formula I by hydrolysis. As examples for such functional carboxlic acid derivatives it is possible to mention: alkyl esters, phenyl esters, benzyl esters, alkoxyalkyl esters dialkylaminoalkyl esters, amides, N-monoalkylamides, N,N-dialkylamides, morpholides, piperidides, piperazides, anilides, N-alkylanilides, N-hydroxyamides, N-alkoxyamides, hydrazides, azides, monothiocarboxylic acids, monothiocarboxylic acid alkyl esters, thioncarboxylic acid alkyl esters, thioamides, thiomorpholides, imideacid ester, amidines, hydrazidines, oxazolines, imidazolines, thiazolines, acid chlorides, acid bromides, acid anhydrides, ketenes and nitriles.

Starting products which, however, are particularly important are those compounds whose production appears advantageous from commercial and economic points of view and which are best described by the general formula II'. If during the hydrolysis the radicals X and Y are eliminated, their chemical structure is, however, of subordinate importance. It is furthermore to be taken into account that a few compounds can be represented by two different formulas owing to possible tautomers (for example amide and imide acids).

As characteristic starting products for the above-mentioned hydrolysis it is possible to mention for example the nitriles, amides and carboxylic acid lower alkyl esters of the general formula II'.

As specific compounds the following come into question for example:
5-chloro-1,3-diphenyl-pyrazole-4-acetonitrile
5-chloro-3-p-chlorophenyl-1-phenyl-pyrazole-4-acetonitrile
5-chloro-3-m-chlorophenyl-1-phenyl-pyrazole-4-acetonitrile
5-chloro-3-p-methoxyphenyl-1-phenyl-pyrazole-4-acetonitrile
5-chloro-1-phenyl-3-p-tolyl-pyrazole-4-acetonitrile
5-chloro-3-p-isobutyl-1-phenyl-pyrazole-4-acetonitrile
5-chloro-3-p-fluorophenyl-1-phenyl-pyrazole-4-acetonitrile
5-bromo-1,3-diphenyl-pyrazole-4-acetonitrile
5-bromo-3-p-fluorophenyl-1-phenyl-pyrazole-4-acetonitrile
5-bromo-3-p-methoxyphenyl-1-phenyl-pyrazole-4-acetonitrile
5-bromo-3-p-isobutylphenyl-1-phenyl-pyrazole-4-acetonitrile
5-bromo-3-p-chlorophenyl-1-phenyl-pyrazole-4-acetonitrile
5-fluoro-1,3-diphenyl-pyrazole-4-acetonitrile
3-p-chlorophenyl-5-fluoro-1-phenyl-pyrazole-4-acetonitrile
5-fluoro-3-p-methoxyphenyl-1-phenyl-pyrazole-4-acetonitrile
5-chloro-3-p-butoxyphenyl-1-phenyl-pyrazole-4-acetonitrile
5-chloro-3-p-chlorophenyl-1-phenyl-pyrazole-4-acetamide
5-chloro-3-p-chlorophenyl-1-phenyl-pyrazole-4-acetic acid methyl ester
5-chloro-3-p-chlorophenyl-1-phenyl-pyrazole-4-acetic acid ethyl ester
5-chloro-3-p-chlorophenyl-1-phenyl-pyrazole-4-acetic acid butyl ester
5-chloro-3-p-chlorophenyl-1-phenyl-pyrazole-4-acetic acid-2-methoxyethyl ester
5-chloro-3-p-chlorophenyl-1-phenyl-pyrazole-4-acetmorpholide
5-chloro-3-p-chlorophenyl-1-phenyl-pyrazole-4-acetanilide
5-chloro-3-p-chlorophenyl-1-phenyl-pyrazole-4 -thioacetmorpholide
5-chloro-3-p-chlorophenyl-1-phenyl-pyrazole-4-acetamidoxime
5-chloro-3-p-chlorophenyl-1-phenyl-pyrazole-4-acetamidinhydrochloride For the hydrolysis of functional carboxylic acid derivatives of the general formula II or II' use is made of a water-delivering medium which consists partly or completely of water or agents which split off water in the conditions of hydrolysis. The reaction can be carried out as a homogeneous reaction in which case the operation is usually carried out in the presence of a polar organic solvent or a solution promotor. Advantageously use can be made as solvents for example of low-molecular weight alcohols, dioxan, acetone, low-molecular weight carboxylic acids, N-methylpyrrolidone, sulfolane or dimethylsulfoxide. Furthermore, however, the hydrolysis can be carried out as a heterogeneous reaction. The pH-value of the water-delivering medium is adjusted in accordance with the chemical nature of the pyrazole-4-acetic acid derivative used, but also in accordance with the nature of the desired compound of the general formula I, and it can therefore be neutral, acidic or basic. It is set with acids, bases or buffers at the desired value.

The hydrolysis temperatures lie between 0° C and the boiling point of the water-delivering medium, generally between 0° and 150° C, and more particularly between 20° and 120° C. The hydrolysis temperatures depend in individual cases also whether the operation is carried out with or without a gauge pressure. The reaction times are in accordance with the batch, reaction temperatures and other reaction parameters between 10 minutes and 20 hours. After the termination of the hydrolysis the pyrazole-4-acetic acids are isolated in accordance with conventional methods, for example by recrystallisation or acidification of their solutions, possibly with the reduction in volume of their solutions. For purifying them, their alkaline solution can be extracted with an organic solvent which is not mixable with the alkaline solution, as for example ether, benzene, chlorobenzene, chloroform or methylene chloride.

The conversion of the pyrazole-4-acetic acids of the general formulae I or I* into their salts can be carried out by direct alkaline hydrolysis of the pyrazole-4-acetic acid derivatives of the general formula II or II'. As an alkaline reaction partner use is made of that inorganic or organic base whose salt it is desired to produce. It is also possible to produce the salts, however, by reacting the pyrazole-4-acetic acids of the general formula I with the stoichiometric equivalent of the corresponding base or converting readily soluble salts by double decomposition into sparingly soluble salts, or converting any desired salts into the pharmacologically compatible salts.

The pyrazole-4-acetic acid derivatives of the general formula II or II′ are in principle accessible using halogenation of 2-pyrazoline-5-ones of the general formula III or IV, which can be obtained in accordance with known or inherently known methods, in the 5-position

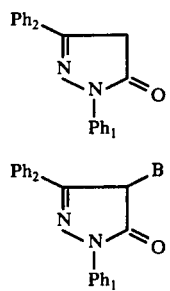

for example with the help of reactive halides of elements of the V and VI Groups of the Periodic System or of reactive carboxylic acid halides, carboxylic acid imide halides or Vilsmeier reagents and possibly via further known method steps.

In accordance with a preferred embodiment of the method a compound of the general formula III is reacted with at least two mole equivalents of a Vilsmeier reagent, which has been produced from a dialkyl- or alkylarylformamide and an acid halide before the reaction or during the reaction in situ to form corresponding 5-halogen-4-pyrazolylmethylene dimethyl ammonium salts, which are then hydrolysed to form 5-halogen-pyrazole-4-carboxaldehydes of the general formula V

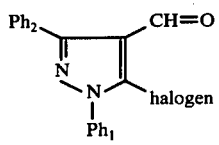

As dialkylformamides use is made for example of dimethylformamide, diethylformamide, diisopropylformamide, N-formylpiperidine, N-formylpiperazine, N,N-diformylpiperazine or N-formylmorpholine. As alkylarylformamides use is made for example of N-methyl-N-phenylformamide or N-ethyl-N-tolylformamide. As acid halides phosphorus oxytrichloride, phosphorus oxytribromide, phosgene and thionyl chloride come preferably into question. In the case of this method, if the reaction is carried out suitably, in addition to the formylation in the 4-position there is also halogenation in the 5-position of the pyrazole with an excellent yield. The reaction temperatures generally lie between 10° and 100° C and the reaction times between 15 minutes and 30 hours.

A further method coming into question is that of halogen exchange, starting from the compounds of the general formula V, for example the substitution of chlorine by bromine or fluorine by means of halides or hydrogen halide acids, possibly at a raised temperature and in a pressure vessel.

Besides the 5-chloro-1,3-diphenyl-pyrazole-4-carboxyaldehyde the compounds of the general formula V are new compounds.

A key intermediate product is the compound 5-chloro-3-p-chlorophenyl-1-phenyl-pyrazole-4-carboxaldehyde, because with this compound 5-chloro-3-p-chlorophenyl-1-phenyl-pyrazole-4-acetic acid and its salts can be prepared and these final products exhibit distinguished pharmacological properties.

The compounds obtained of the general formula V are converted by means of methods known as such (see for example the Belgian patent specification 755,924) via a series of intermediate stages to form the pyrazole-4-acetic acid derivatives of the general formula II. Thereby the carbonyl group is reduced under mild conditions to form a hydroxymethyl group which is converted into a halogen methyl or trialkylammonium methyl group which is reacted with a cyanide to form nitriles of the general formula II. The reduction can be carried out for example with sodium borohydride in an anhydrous or water-containing solvent between 0° and 50° C. The halogen methyl compounds can be obtained from the hydroxymethyl compounds for example by reaction with sulfur or phosphorus halides or carboxylic acid halides, such as phosgene, but also by reaction with hydrogen halide acids and their concentrated aqueous solutions, in the case of which any suitable inert solvents can come into question. The reaction of the 4-halogen-methyl-5-halogen-pyrazoles to form nitriles of the general formula II can be carried out in accordance with the methods described in the Belgian patent specification No. 755,925 for similar compounds, preferably in aprotic, dipolar solvents, at temperatures between 0° and 80° C.

Pyrazole-4-acetic acid esters of the general formula II can readily be obtained from other reactive pyrazole-4-acetic acid derivatives of the general formula II in accordance with conventional methods, for example from acid halides, acid anhydrides and nitriles by alcoholysis, and furthermore from pyrazole-4-acetic acids of the general formula I by reaction with alcohols under conditions leading to the slitting off of water or by reaction of acids and salts with alkylating agents, as for example of benzyl esters by reaction of alkali metal salts with benzyl halides.

Unsubstituted amides of the general formula II can be produced by hydrolysis of corresponding nitriles. The aminolysis of reactive carboxylic acid derivatives as for example acid halides or esters with ammonia, with mono or dialkylamines with arylamines, cyclic amines, such as piperidine, morpholine and piperazine, with hydroxylamine, O-alkyl-hydroxylamine and with, possibly, substituted hydrazines provides, if required, -N-alkyl or aryl substituted amides, piperidides, morpholides, piperazides and furthermore hydroxamic acids, O-alkylamides and, if required, N-alkyl or aryl substituted hydrazides of the general formula II.

Thioamides of the general formula II can for example be produced by reaction of nitriles and hydrogen sulfide in the presence of bases or by the sulfurisation of amides, for example with phosphorus pentasulfide.

To the nitriles of the general formula II furthermore alcohols can be added on acidic catalysis to form the corresponding imide acid esters while the nitriles react with arylamines with basic catalysts to form corresponding amidines and they react with mercaptans or mercaptoacetic acid to form corresponding thioimide acid esters.

From imide acid esters of the general formula II it is for example possible to produce amidines with amines, oxazolines with amino alcohols and imidazolines with diamines.

Acid halides of the general formula II can be produced in a conventional manner from the compounds of formula I by means of halides of the phosphorus or sulfur acids and ketenes can be produced from the acid halides by dehydrohalogenation by means of tertiary organic bases.

It has been found as a matter of experience that in many cases for the intermediate products II or II' and their preliminary stages no special purification operations were necessary and that they can be used without following purification steps in the next method step following.

It has been found, surprisingly, that the compounds of formula I and their salts, while having a comparatively low toxicity, have pronounced antiphlogistic and also analgesic and antipyretic lowering properties.

In particular the antiinflammatory action could be shown to exist after single and multiple administration in acute and chronic inflammation experiments as well. The compounds of this invention exhibited a high superiority over compounds known in the art as shown in table 1 in comparison with the commercially available medicament phenyl butazone (I) for example by 5-chloro-3-p-chlorophenyl-1-phenyl-pyrazol-4-acetic acid (II) and 5-chloro-1,3-diphenyl-pyrazol-4-acetic acid (III).

was determined on the retarding inflammation at the carrageenin edema of the rear paw of the rat [Winter et al. Proc. Soc. exp. Biol. Med. 111 (1962) 544], wherein in table 2 those doses are shown which cause a mean retardation of 25% 3 and 5 hours after single administration of the substance to be tested; on the retardation at the ultraviolet erythema of the skin on the back of the guinea pig [Winder et al. Arch. int. Pharmacodyn. 116 (1958) 261], wherein in table 1 those doses are shown which cause a retardation of 25% 5 hours after irradiation; on a chronic inflammation model (cotton granuloma) wherein the influence of the compounds on the granulation tissue formation after subcutaneous implantation of cotton plugs in rats was studied after daily administration on 7 following days in taking pattern from the method described by Winter et al. [J. Pharmacol. exp. Therap. 141 (1963) 369], in table 1 those doses are shown which inhibit the reformation of the granulation tissue by 20% ($ED_{20}$).

The lethal doses were determined in usual manner. $LD_{50}$ (mice) and $LD_5$ (rats), respectively, denote the dose at which 50% and 5% of the animals, respectively, died within 10 days after single and 7 days administration, respectively, of the substance.

In the case of the application of a therapeutically-effective and pharmacologically-compatible quantity the compounds in accordance with the invention are therefore suitable for the treatment of a large number of disease conditions of mammals, in the case of which one or more symptoms of inflammation, pains and fever occur. Examples of such disease conditions are the most various different inflammatory and degenerative dis- Table 1

Antiphlogistic activity, lethal dosis ($LD_5$) and therapeutic index Q of halogenopyrazol derivatives

| Compound | Retardation of the UV-Erythema [$ED_{25}$] [mg/kg]p.o. | relative effect | Retardation of the granulation tissue formation [$ED_{20}$] [mg/kg/die] 7 × p.o. | relative effect | $LD_5$ [mg/kg/die] 7 × p.o. | Q $LD_5/ED_{20}$ |
|---|---|---|---|---|---|---|
| I | 1 | 1,0 | 100 | 1.0 | 150 | 1.5 |
| II | 0.15 | 6.7 | 3 | 33.3 | 18 | 6.0 |
| III | 0.25 | 4.0 | 8 | 12.5 | 100 | 12.5 |

However, the compounds in accordance with the invention also showed a specific action and a degree of superiority, for example also with regard to their therapeutic breadth, as compared with the above-mentioned standard preparation (I) in another form of pharmacological tests, as shown in table 2 for example by the following compounds:

5-chloro-3-p-chlorophenyl-1-phenyl-pyrazole-4-acetic acid (II), 5-chloro-1,3-diphenyl-pyrazole-4-acetic acid (III) and 5-chloro-3-p-methoxyphenyl-1-phenyl-pyrazole-4-acetic acid (IV).

Table 2

Antiphlogistic activity, acute toxicity ($LD_{50}$) and therapeutic index Q of halogeno-pyrazole derivatives.

| Compound | Retardation of the Carrageenin Edema ($ED_{25}$) [mg/kg]p.o. | relative effect | $LD_{50}$ [mg/kg]p.o. | Q $LD_{50}/ED_{25}$ |
|---|---|---|---|---|
| I | 10 | 1.0 | 635 | 63.5 |
| II | 1.5 | 6.7 | 530 | 353 |
| III | 1.0 | 10.0 | 1200 | 1200 |
| IV | 12 | 0.8 | 1100 | 91.7 |

The antiinflammatory action of the standard preparation and the compounds of this invention, respectively, eases of the rheumatic form circle and other inflammatory disease processes, for example acute and chronic polyarthritis, osteoarthritis, psoriatic arthritis, ankylosespondylitis, polyarthroses, spondyloses, rheumatism of the joints, rheumatic fever; rheumatism of soft parts as for example tendinitis, periarthritis and periostitis; acute muscular rheumatism, for example ischias; painful postoperative swellings and inflammation; pains and swellings after bruising of the joints, sprains and fractures; pains and inflammation connected with dental surgery; pain conditions of the most various different origins, for example neuritides, headaches and spasms; and also human and animal disease conditions which give rise to the above symptoms and make necessary the use of an inflammation-preventing analgesic and/or antipyretic medicament.

A further form of subject matter of the invention is therefore a method for the treatment of mammals, which are suffering from one or more of the above symptoms of inflammation, pain or fever. The method is characterised by administering a therapeutically-effective and pharmacologically-compatible quantity of one or more compounds of the general formula I and/or their salts to the diseased mammal.

The invention furthermore therefore comprises also medicinal substances which are characterised by a content of one or more of the new active substances. Possibly the new medicaments contain pharmaceutical vehicle materials, in addition to the new active substances, for the latter. The active substance content of these medicaments amounts to between 1 and 95 % by weight and preferably between 10 and 85% by weight, expressed in terms of the finished medicament.

The medicaments are preferably administered orally, rectally, as solutions of salts parenterally, for example subcutaneously, intramuscularly or intravenously by injection or topically (percutaneously). Preferably the pharmaceutical preparation of the active substance is in the form of unitary doses, which are matched to suit the desired administration. A unitary dose can be, for example, a tablet, a capsule, a suppository or a measured volume quantity of a powder, a granulate, a solution, an emulsion, a suspension or a gel or of an ointment. The term "unitary dose" within the meaning of the present invention is to be understood to mean a physically determined unit, which comprises the individual quantity of the active component mixed with a pharmaceutical diluent for it or together with a pharmaceutical vehicle material. In this respect the quantity of the active substance is so selected that one or more units are conventionally required for a single therapeutic administration.

The unitary dose can, however, also be capable of being split up, for example in the form of tablets provided with notches, if for the individual therapeutic administration only a fraction, as for example a half or a quarter, of the unit which can be subdivided is required.

The pharmaceutical preparations in accordance with the present invention comprise, if they are produced as unitary doses, 1 to 1000 mg, and with more particularly advantageous effects approximately 5 to 500 mg and more particularly approximately 10 to 250 mg of active substance. The therapeutic administration of the pharmaceutical preparations can be carried out 1 to 4 times daily, for example respectively after the mealtimes and-/or in the evening. The dose which is administered is determined in accordance with the frequency of the administration, the duration of treatment, the nature and severity of the illness, and in accordance with the weight, age and the general condition of health of the patient. The daily dose generally lies between 0.05 and 70 mg/kg body weight for mammals.

The pharmaceutical preparations consist generally of the active substances in accordance with the invention and non-toxic pharmaceutically-acceptable medicament vehicles, which are used as an addition to the mixture in the form of solid, semi-solid or liquid materials or as encasing means, for example in the form of a capsule, of a tablet coating, of a bag or another container, which come into question for the therapeutically-active component. A vehicle material can serve for example as a promoter for the take up of the medicament by the body, as an adjuvant for formulation, as a sweetening agent, as a flavoring material, as a dye or as a preserving agent.

For oral administration it is possible to use for example tablets, dragees, hard and soft capsules, for example of gelatin, dispersible powders, granulates, aqueous and oily suspensions, emulsions, solutions or sirups.

Tablets can comprise inert diluents, for example calcium carbonate, calcium phosphate, sodium phosphate or lactose; granulation and distributing agents, as for example maize starch or alginates; binding agents, as for example starch, gelatin or acacia gum; and lubricants, as for example aluminum or magnesium stearate, talc or silicone oil. They can be additionally provided with a coating, which can be so made that it brings about a delay in breaking up and resorption of the medicament in the gastrointestinal tract and thus an improved compatibility or a longer period of action for example. Gelatin capsules can be used to hold the medicament mixed with a solid agent, such as calcium carbonate or kaolin or an oil diluting agent, such as olive, ground nut or liquid paraffin oil.

Aqueous suspensions can comprise suspending agents, as for example sodium carboxymethylcellulose, methylcellulose, hydroxypropylcellulose, sodium alginate, polyvinylpyrrolidone, gum traganth or acacia gum; dispersing and wetting agents, such as polyoxyethylene stearate, heptadecaethyleneoxycetanol, polyoxyethylenesorbitol monooleate, polyoxyethylenesorbitane monooleate or lecithin; preserving agents, as for example methyl or propylhydroxybenzoate; flavoring agents; sweeting agents, as for example saccharose, lactose, dextrose, invert sugar sirup.

Oily suspensions can comprise for example ground nut, olive, sesame, coconut or paraffin oil and thickening agents, as for example beeswax, paraffin wax or cetylalcohol; and furthermore sweetening agents, flavoring agents and antioxidants.

Powders and granulates which can be dispersed in water can comprise the medicaments in admixture with dispersing, wetting and suspending agents, for example the above-mentioned ones and with sweetening agents, flavoring agents and dyes.

Emulsions can comprise for example olive, ground nut or paraffin oil in addition to emulsifying agents as for example acacia gum, gum traganth, phosphatides, sorbitane monooleate, polyoxyethylenesorbitane monooleate, sweetening and flavoring agents.

For rectal application of the medicinal substances it is possible to use suppositories, which can be produced with the help of binding agents fusing at rectal temperatures, for example cacao butter or polyethyleneglycols.

For parenteral application of the medicaments it is possible to use sterile injection aqueous suspensions, isotonic salt solutions or other solutions, which can comprise dispersing and/or wetting agents and/or pharmacologically-compatible diluting agents, as for example propylene or butyleneglycol.

In addition to the novel pyrazole-4-acetic acids the pharmaceutical preparations can comprise for example one or more pharmacologically-active components from other groups of medicaments as for example corticosteroids acting to suppress inflammation (as for example prednisone, predinisolone, dexamethasone and their derivatives); analgesics, as for example pyrazolone derivatives (for example aminophenazone), propoxyphene, phenacetin, salicylic acid derivatives, etc.; muscle relaxants, as for example pyridizine derivatives, carbamates (for example phenprobamate) etc.; substances with an antiulcerogenic action; antacid materials (as for example magnesium trisilicate and aluminium hydroxide); substances encouraging local blood circulation as for example nicotinic acid derivatives and dimethylsulfoxide; local anesthetics (as for example lidocain) and vitamins (as for example vitamin-$B_1$-chloride-hydrochloride, vitamin-$B_6$-hydrochloride, vitamin-$B_{12}$-cyano complex and thiamin disulfide).

The following examples explain the invention in more detail without restricting it. The temperatures mentioned are given in ° C. the abbreviation F denotes the melting point, the abbreviation $Kp_{10}$ the boiling point at 10 Torr.

EXAMPLE 1

5-Chloro-1,3-diphenyl-pyrazole-4-acetic acid 19.1 g of 5-chloro-1,3-diphenyl-pyrazole-4-acetonitrile are heated in 96 g of 63 percent sulfuric acid for 1 hour at 115° C. The solution is cooled and the acid is precipitated by diluting with 500 ml of water and it is washed with water and crystallised from ethanol and water. A product containing water of crystallisation is obtained which after dissolving in benzene and reduction in volume of the solution is dehydrated. With the yield of 91% 5-chloro-1,3-diphenyl-pyrazole-4-acetic acid is obtained; F 151°–152°.

EXAMPLE 2

5-Chloro-3-p-chlorophenyl-1-phenyl-pyrazole-4-acetic acid 30 g of 5-chloro-3-p-chlorophenyl-1-phenyl-pyrazole-4-acetonitrile and a mixture of 46 ml of concentrated sulfuric acid and 55 ml water are heated for 2.5 hours while stirring at 100° C. Then the solution is diluted with 700 ml of water, the precipitate is drawn off and washed with water. The filter cake is dissolved in diluted sodium hydroxide and purified with active charcoal and the acid is precipitated with diluted hydrochloric acid. 5-Chloro-3-p-chlorophenyl-1-phenyl-pyrazole-4-acetic acid is obtained with a yield of 95%; F 179.5°–181° (from methanol).

From the corresponding pyrazole-4-acetonitriles
5-chloro-3-p-methoxyphenyl-1-phenyl-pyrazole-4-acetonitrile
5-chloro-1-phenyl-3-p-tolyl-pyrazole-4-acetonitrile
5-chloro-3-m-chlorophenyl-1-phenyl-pyrazole-4-acetonitrile
5-chloro-3-p-isotutylphenyl-1-phenyl-pyrazole-4-acetonitrile
5-bromo-1,3-diphenyl-pyrazole-4-acetonitrile
5-bromo-3-p-chlorophenyl-1-phenyl-pyrazole-4-acetonitrile
5-bromo-3-p-methoxyphenyl-1-phenyl-pyrazole-4-acetonitrile
3-p-bromophenyl-5-chloro-1-phenyl-pyrazole-4-acetonitrile the following compounds
5-chloro-3-p-methoxyphenyl-1-phenyl-pyrazole-4-acetic acid (F 166.5°–167.5°)
5-chloro-1-phenyl-3-p-tolyl-pyrazole-4-acetic acid
5-chloro-3-m-chlorophenyl-1-phenyl-pyrazole-4-acetic acid
5-chloro-3-p-isobutylphenyl-1-phenyl-pyrazole-4-acetic acid (F 110°–110.3°)
5-bromo-1,3-diphenyl-pyrazole-4-acetic acid (F 187.5°–188.5°)
5-bromo-3-p-chlorophenyl-1-phenyl-pyrazole-4-acetic acid
5-bromo-3-p-methoxyphenyl-1-phenyl-pyrazole-4-acetic acid
3-p-bromophenyl-5-chloro-1-phenyl-pyrazole-4-acetic acid are obtained in a similar manner.

EXAMPLE 3

5-Chloro-3-p-chlorophenyl-1-phenyl-pyrazole-4-acetic acid 3.8 g of ethyl 5-chloro-3-p-chlorophenyl-1-phenyl-pyrazole-4-acetate, 13 ml of ethanol and 1.0 g of sodium hydroxide are heated in 13 ml of water for 1 hour for boiling. The pH is reduced to 10 and the alcohol is distilled off in vacuo. The aqueous solution is shaken up with ether and purified with active charcoal. Acidification is carried out with dilute hydrochloric acid and with a yield of 83% 5-chloro-3-p-chlorophenyl-1-phenyl-pyrazole-4-acetic acid is obtained; F 179.5°–181°.

In a similar manner it is possible to produce from
methyl 5-chloro-3-p-chlorophenyl-1-phenyl-pyrazole-4-acetate
n-butyl 5-chloro-3-p-chlorophenyl-1-phenyl-pyrazole-4-acetate
n-hexyl 5-chloro-3-p-chlorophenyl-1-phenyl-pyrazole-4-acetate
benzyl 5-chloro-3-p-chlorophenyl-1-phenyl-pyrazole-4-acetate
phenyl 5-chloro-3-p-chlorophenyl-1-phenyl-pyrazole-4-acetate
3-ethoxyethyl 5-chloro-3-p-chlorophenyl-1-phenyl-pyrazole-4-acetate
3-dimethylaminoethyl 5-chloro-3-p-chorophenyl-1-phenyl-pyrazole-4-acetate
ethyl 5-chloro-3-p-chlorophenyl-1-phenyl-pyrazole-4-thioacetic using alkaline hydrolysis
5-chloro-3-p-chlorophenyl-1-phenyl-pyrazole-4-acetic acid (F 179.5°–181°).

In a similar manner it is possible to produce from
methyl-5-chloro-3-p-chlorophenyl-1-phenyl-pyrazole-4-acetate
n-butyl 5-chloro-3-p-chlorophenyl-1-phenyl-pyrazole-4-acetate
n-hexyl 5-chloro-3-p-chlorophenyl-1-phenyl-pyrazole-4-acetate
benzyl 5-chloro-3-p-chlorophenyl-1-phenyl-pyrazole-4-acetate
phenyl 5-chloro-3-p-chlorophenyl-1-phenyl-pyrazole-4-acetate
3-ethoxyethyl 5-chloro-3-p-chlorophenyl-1-phenyl-pyrazole-4-acetate
3-dimethylaminoethyl 5-chloro-3-p-chlorophenyl-1-phenyl-pyrazole-4-acetate
ethyl 5-chloro-3-p-chlorophenyl-1-phenyl-pyrazole-4-thioacetic using alkaline hydrolysis
5-chloro-3-p-chlorophenyl-1-phenyl-pyrazole-4-acetic acid (F 179.5°–181°).

In a similar manner it is possible to produce from
ethyl 5-chloro-1,3-diphenyl-pyrazole-4-acetate
methyl 5-chloro-3-p-methoxyphenyl-1-phenyl-pyrazole-4-acetate
methyl 5-bromo-1,3-diphenyl-pyrazole-4-acetate by alkaline hydrolysis
5-chloro-1,3-diphenyl-pyrazole-4-acetic acid (F 151°–152°)
5-chloro-3-p-methoxyphenyl-1-phenyl-pyrazole-4-acetic acid (F 166.5°–167.5°)
5-bromo-1,3-diphenyl-pyrazole-4-acetic acid (F 187.5°–188.5°).

EXAMPLE 4

5-Chloro-3-p-chlorophenyl-1-phenyl-pyrazole-4-acetic acid 1.0 g of 5-chloro-3-p-chlorophenyl-1-phenyl-pyrazole-4-acetonitrile, 10 ml of ethanol and 1.4 g of sodium hydroxide are heated at boiling point for 4 hours until the evolution of ammonia is terminated. The alcohol is distilled in vacuo, treated with ether, purified with active charcoal and the aqueous phase is acidified with hydrochloric acid to pH 3. With a yield of 95% 5-chloro-3-p-chlorophenyl-1-phenyl-pyrazole-4-acetic acid is obtained; F 179.5°–181°.

EXAMPLE 5

5-Chloro-3-p-chlorophenyl-1-phenyl-pyrazole-4-acetic acid 2.0 g of 5-chloro-3-p-chlorophenyl-1-phenyl-pyrazole-4-acetamide and 10 g of 63 % sulfuric acid are heated for 1.5 hours at 100° C and prepared in accordance with example 2.5-Chloro-3-p-chlorophenyl-1-phenyl-pyrazole-4-acetic acid is obtained: F 179.5°–181°.

In a similar manner it is possible to produce from 5-chloro-3-p-chlorophenyl-1-phenyl-pyrazole-4-acetic acid-n-butylamide
5-chloro-3-p-chlorphenyl-1-phenyl-pyrazole-4-acetic acid-diethylamide
5-chloro-3-p-chlorophenyl 1-phenyl-pyrazole-4-acet-morpholide
5-chloro-3-p-chlorophenyl-1-phenyl-pyrazole-4-acet-piperidide
5-chloro-3-p-chlorophenyl-1-phenyl-pyrazole-4-acet-pyrrolidide
5-chloro-3-p-chlorophenyl-1-phenyl-pyrazole-4-acetanilide
5-chloro-3-p-chlorophenyl-1-phenyl-pyrazole-4-acetic acid-N-methylanilide
5-chloro-3-p-chlorophenyl-1-phenyl-pyrazole-4-acethydroxamic acid
5-chloro-3-p-chlorophenyl-1-phenyl-pyrazole-4-acetamidoxime
5-chloro-3-p-chlorophenyl-1-phenyl-pyrazole-4-acethydrazide
5-chloro-3-p-chlorophenyl-1-phenyl-pyrazole-4-acetamidine-hydrochloride by hydrolysis with sulfuric acid
5-chloro-3-p-chlorophenyl-1-phenyl-pyrazole-4-acetic acid (F 179.5°–181° ).

EXAMPLE 6

5-Chloro-3-p-chlorophenyl-1-phenyl-pyrazole-4-acetic acid 0.3 g of 5-chloro-3-p-chlorophenyl-1-phenyl-pyrazole-4-thioacetmorpholide and 6 ml of 20 % hydrochloric acid are heated at boiling point until the evolution of hydrogen sulfide is finished. 5-Chloro-3-p-chlorophenyl-1-phenyl-pyrazole-4-acetic acid is obtained; (F 179.5°–181° ).

In a similar manner it is possible to produce from 5-chloro-3-p-chlorophenyl-1-phenyl-pyrazole-4-acetimideethyl ester hydrochloride
2-[(5-chloro-3-p-chlorophenyl-1-phenyl-4-pyrazolyl)-methyl]-oxazoline
2-[(5-chloro-3-p-chlorophenyl-1-phenyl-4-pyrazolyl)-methyl]-thiazoline
1-methyl-2-[(5-chloro-3-p-chlorophenyl-1-phenyl-4-pyrazolyl)-methyl]-imidazoline by hydrolysis with hyrochloric acid
5-chloro-3-p-chlorophenyl-1-phenyl-pyrazole-4-acetic acid (F 179.5°–181° ).

EXAMPLE 7

5-Chloro-3-p-chlorophenyl-1-phenyl-pyrazole-4-acetic acid 3.5 g of 5-chloro-3-p-chlorophenyl-1-phenyl-pyrazole-4-acetamide are dissolved in 15 ml of 90 % sulfuric acid and while stirring at 20° to 30° a solution of 0.7 g sodium nitrite in a little water is passed dropwise under the surface. Gentle heating is carried out until the evolution of gas is terminated and the mixture is then poured on to an ice and water mixture. 5-Chloro-3-p-chlorophenyl-1-phenylpyrazole-4-acetic acid is produced; F 179.5°–181°.

EXAMPLE 8

Sodium salt of 5-chloro-3-p-chlorophenyl-1-phenyl-pyrazole-4-acetic acid 3.5 3-p-chlorophenyl-of 5-chloro-3-p-chlorophenyl-1-phenyl-pyrazole-4-acetic acid are dissolved in 10 ml of 1/10 N sodium hydroxide, the solution is evaporated in vacuo to dryness and the residue is taken up with ether. The sodium salt of 5-chloro-3-p-chlorophenyl 1-phenyl-pyrazole-4-acetic acid is obtained; F 275°–279°.

EXAMPLE 9

Calcium salt of 5-chloro-3-p-chlorophenyl-1-phenyl-pyrazole-4-acetic acid

A solution of 3.5 g of 5-chloro-3-p-chlorophenyl-1-phenyl-pyrazole-4-acetic acid in the equivalent quantity of diluted sodium hydroxide is added dropwise at a raised temperature to a solution of 1.6 g of calcium chloride hexahydrate in 12 ml of water. The precipitate is washed with diluted calcium chloride solution and ice-cold water. The calcium salt of 5-chloro-3-p-chlorophenyl-1-phenyl-pyrazole-4-acetic acid is obtained with a quantitative yield: F 302°–307° (decomposition).

EXAMPLE 10

Morpholine salt of 5-chloro-3-p-chlorophenyl-1-phenyl-pyrazole-4-acetic acid

To a solution of 1.0 g of 5-chloro-3-p-chlorophenyl-1-phenyl-pyrazole-4-acetic acid in 45 ml of ether 0.25 g of morpholine is added, dropwise. The morpholine salt of 5-chloro-3-p-chlorophenyl-1-phenyl-pyrazole-4-acetic acid is obtained with a 87 % yield; F 144°–145°.

EXAMPLE 11

5-Chloro-1,3-diphenyl-pyrazole-4-carboxaldehyde

At 5° to 10° 97.3 g of phosphorus oxytrichloride are added dropwise to 92.7 g of dimethylformamide and the mixture is stirred for completion of the complex formation for 30 minutes at room temperature. Following this 30 g of 1,3-diphenyl-2-pyrazole-5-one are added and while stirring heating is carried out for 1 hour at 55° C and for 20 hours at 70°. The product is poured on to approximately 600 g of ice neutralised with concentrated sodium hydroxide solution to pH 3-4, vacuum filtered and washed with water. 5-Chloro-1,3-diphenyl-pyrazole-4-carboxaldehyde is obtained with a yield of 93 %; F 109°–110° (from petroleum ether).

EXAMPLE 12

5-Chloro-3-p-chlorophenyl-1-phenyl-pyrazole-4-carboxaldehyde a. At 5 to 10° 284 g of phosphorus oxytrichloride are added dropwise during a period of 90 minutes to 270 g of dimethylformamide. Stirring is carried out for 30 minutes at 15° and then 100 g of 3-p-chlorophenyl-1-phenyl-2-pyrazoline-5-one are added. Heating is carried out for 1.5 hours at 50° and for 21 hours at 70°. The product is poured on to 2 kg of ice, the pH is adjusted to 3-4 with 20 % of sodium hydroxide and the precipitate is filtered off. 5-Chloro-3-p-chlorophenyl-1-phenyl-pyrazole-4-carboxaldehyde is obtained with a yield of 99 %; F 169°-171° (from acetone).

In accordance with procedure (a) from the corresponding 2-pyrazoline-5-ones the following
5-chloro-3-p-methoxyphenyl-1-phenyl-pyrazole-4-carboxaldehyde (F 108°-10°)
5-chloro-3-m-chlorophenyl-1-phenyl-pyrazole-4-carboxaldehyde
5-chloro-1-phenyl-3-p-tolyl-pyrazole-4-carboxaldehyde
5-chloro-3-p-isobutylphenyl-1-phenyl-pyrazole-4-carboxaldehyde (F 56.5°-57°)
5-chloro-3-p-fluorophenyl-1-phenyl-pyrazole-4-carboxaldehyde
3-p-bromophenyl-5-chloro-1-phenyl-pyrazole-4-carboxaldehyde are prepared.

b. The 3-p-chloro-phenyl-1-phenyl-2-pyrazoline-5-one required as a starting product is produced in the following manner:

50.8 g of ethyl p-chlorobenzoylacetate (produced for example from p-chloroacetophenone, diethyl carbonate and sodium hydride with a yield of 72 %) 29 g of phenylhydrazine, 5 ml of glacial acetic acid and 150 ml of ethanol are heated in a nitrogen atmosphere for 1 hour at boiling point. After cooling in an ice bath 3-p-chlorophenyl-1-phenyl-2-pyrazoline-5-one is obtained with a yield of 84 %; F 160.5°-161.5°.

In accordance with procedure (b) the following 2-pyrazoline-5-ones are obtained:
3-p-methoxyphenyl-1-phenyl-2-pyrazoline-5-one (F 137°-138°)
3-m-chlorophenyl-1-phenyl-2-pyrazoline-5-one
1-phenyl-3-p-tolyl-2-pyrazoline-5-one
3-p-isobutylphenyl-1-phenyl-2-pyrazoline-5-one (F 124.5°-125°)
3-p-fluorophenyl-1-phenyl-2-pyrazoline-5-one
3-p-bromophenyl-1-phenyl-2pyrazoline-5-one

EXAMPLE 13

5-Bromo-1,3-diphenyl-pyrazole-4-carboxaldehyde 175 g of fused phosphorus oxytribromide are added dropwise in a period of 75 minutes while stirring and cooling at 10°-16° to 306 g of dimethylformamide. To the crystal suspension of the Vilsmeier complex 29 g of 1,3-diphenyl-2-pyrazoline-5-one are added and heating is then carried out for 20 hours at 65° to 70°. The product is poured on to 850 g of ice, the pH is adjusted with 2 n sodium hydroxide solution to 4-5. Vacuum filtration is carried out and the precipitate is well washed with water. Raw
5-bromo-1,3-diphenylpyrazole-4-carboxaldehyde is obtained with an 85 yield and is purified by filtration of a chloroform solution over silica gel; F 128°-128.5°.

In similar manner it is possible to produce from 3-p-chlorophenyl-1-phenyl-2-pyrazoline-5-one
3-p-methoxyphenyl-1-phenyl-2-pyrazoline-5-one and the Vilsmeier complex from phosphorus oxytribromide and dimethylformamide
5-bromo-3-p-chlorophenyl-1-phenyl-pyrazole-4-carboxaldehyde (F 178°-179.5°)
5-bromo-3-p-methoxyphenyl-1-phenyl-pyrazole-4-carboxaldehyde.

EXAMPLE 14

5-Chloro-4-hydroxymethyl-1,3-diphenyl-pyrazole

To a solution of 21 g of 5-chloro-1,3-diphenyl-pyrazole -4-carboxaldehyde in 80 ml of dioxan there is added dropwise at 23° to 27° a solution of 1.11 g of sodium borohydride in 35 ml of water. The resulting suspension is stirred for a further 30 minutes and on the addition of 200 ml of water 5-chloro-4-hydroxymethyl-1,3-diphenyl-pyrazole is precipitated with a 99 % yield; F 140.5°-141.5° (from toluene).

EXAMPLE 15

5-Chloro-3p-chlorophenyl-4-hydroxymethyl-1-phenyl-pyrazole 2.8 g of sodium borohydride are added to a suspension of 46.4 g of 5-chloro-3-p-chlorophenyl-1-phenyl-pyrazole-4-carboxaldehyde in 700 ml of dimethylformamide and 100 ml of water, the temperature possibly rising to 35°. After 30 minutes purification is carred out with active charcoal, precipitation is carried out with 700 ml of water and the precipitate is well washed. 5-Chloro-3-p-chlorphenyl-4-hydroxymethyl-1-phenyl-pyrazole is obtained with a 95 % yield; F 152.5°-153.5° (from acetone).

In a similar manner it is possible to obtain from the corresponding pyrazole-4-carboxaldehydes by reduction
5-chloro-4-hydroxymethyl-3-p-methoxyphenyl-1-phenylpyrazole (F 126°-127°)
5-chloro-4-hydroxymethyl-1-phenyl-3-p-tolyl-pyrazole
5-chloro-3-m-chlorophenyl-4-hydroxymethyl-1-phenyl-pyrazole
5-chloro-4-hydroxymethyl-3-p-isobutylphenyl-1-phenylpyrazole (F 140°-140.4°)
5-bromo-4-hydroxymethyl-1,3-diphenyl-pyrazole (F 134°-135°)
5-bromo-3-p-chlorophenyl-4-hydroxymethyl-1-phenyl-pyrazole
5-bromo-4-hydroxymethyl-3-p-methyloxyphenyl-1-phenyl-pyrazole
3-p-bromophenyl-5-chloro-4-hydroxymethyl-1-phenyl-pyrazole

EXAMPLE 16

5-Chloro-4-chloromethyl-3-p-chlorophenyl-1-phenyl-pyrazole 17.6 g of thionyl chloride are added to a suspension of 45 g of 5-chloro-3-p-chlorophenyl-4-hydroxymethyl-1-phenyl-pyrazole in 45 ml of benzene, there being a considerable evolution of gas and solution occurs. Following this heating is carried out for 30 minutes at boiling point for completion of the reaction. The solvent is distilled off in vacuo and this operation is carried out with the addition of benzene. The residue is caused to crystallise with the help of petroleum ether. 5-Chloro-4-chloromethyl-3-p-chlorophenyl-1-phenyl-pyrazole is obtained with a 98.5% yield; F 9.6°-97°.

In a similar manner it is possible to obtain from the corresponding 4-hydroxymethyl-pyrazoles the following 4-chloromethyl-pyrazoles
5-chloro-4-chloromethyl-1,3-diphenyl-pyrazole (F 67.5°-68.5°)
5-chloro-4-chloromethyl-3-p-methoxyphenyl-1-phenyl-pyrazole (F 129°-129.5°)
5-chloro-4-chloromethyl-1-phenyl-3-p-tolyl-pyrazole 5-chloro-4-chloromethyl-3-m-chlorophenyl-1-phenyl-pyrazole 5-chloro-4-chloromethyl-3-p-isobutylphenyl-1-phenyl-pyrazole (F 87°–87.3°)

5-bromo-4-chloromethyl-1,3-diphenyl-pyrazole (F 83.5°–84°)

5-bromo-4-chloromethyl-3-p-chlorophenyl-1-phenyl-pyrazole 5-bromo-4-chloromethyl-3-p-methoxyphenyl-1-phenyl-pyrazole 3-p-bromophenyl-5-chloro-4-chloromethyl-1-phenyl-pyrazole

EXAMPLE 17

5-Chloro-4-chloromethyl-3-p-chlorophenyl-1-phenyl-pyrazole

Hydrogen chloride gas is introduced into a mixture of 15 g of 5-chloro-3-p-chlorophenyl-4-hydroxymethyl-1-phenylpyrazole and 25 ml of concentrated hydrochloric acid and heating is carried out for 4 hours at boiling point. Following this 25 ml of toluene are mixed in. The layers are separated and the aqueous phase with toluene is removed. The organic layers are reduced in bulk by evaporation in vacuo, toluene is again added and reduction in bulk is repeated. 5-Chloro-4-chloromethyl-3p-chlorophenyl-1-phenyl-pyrazole is obtained with a quantitative yield; F 96.5°–97° (from petroleum ether).

EXAMPLE 18

5-Chloro-3-p-chlorophenyl-1-phenyl-pyrazole-4-acetonitrile 35 g of 5-chloro-4-chloromethyl-3-p-chlorophenyl-pyrazole are added while stirring and slight cooling at 25° to a mixture of 6.15 g of sodium cyanide in 150 ml of dimethylsulfoxide. Stirring is carried out for 2 to 5 hours at this temperature until the reaction is determined. The solution is mixed with 200 ml of water and 200 ml of trichloroethylene or benzene. The layers are separated. Washing is carried out with the organic solvent. Drying is carried out with sodium sulfate and the organic phase is purified with Tonsil. By reducing in bulk in vacuo 5-chloro-3-p-chlorophenyl-1-phenyl-pyrazole-4-acetonitrile is obtained with a yield equal to 99 % of the theoretical amount; F 129.5°–130.5° (from acetonitrile).

In a similar manner it is possible to obtain for the corresponding 4-chloromethyl-pyrazoles the following pyrazole-4-acetonitriles:

5-chloro-1,3-diphenyl-pyrazole-4-acetonitrile (F 78.5°–79.5°)

5-chloro-3-p-methoxyphenyl-1-phenyl-pyrazole-4-acetonitrile (F 91.5°–92.5°)

5-chloro-1-phenyl-3-p-tolyl-pyrazole-4-acetonitrile 5-chloro-m-chlorophenyl-1-phenyl-pyrazole-4-acetonitrile 5-chloro-3-p-isobutylphenyl-1-phenyl-pyrazole-4-acetonitrile (F 98°–98.5°)

5-bromo-1,3-diphenyl-pyrazole-4-acetonitrile (F 99°–100.5°)

5-bromo-3-p-chlorophenyl-1-phenyl-pyrazole-4-acetonitrile 5-bromo-3-p-methoxyphenyl-1-phenyl-pyrazole-4-acetonitrile 3-p-bromophenyl-5-chloro-1-phenyl-pyrazole-4-acetonitrile

EXAMPLE 19

Ethyl 5-chloro-3-p-chlorophenyl-1-phenyl-pyrazole-4-acetate 10 g of 5-chloro-3-p-chlorophenyl-1-phenyl-pyrazole-4-acetonitrile, 100 ml of ethanol, 1.5 ml of water and 15 ml of concentrated sulfuric acid are heated for 16 hours at boiling point. The liquid is poured on to ice, made alkaline with sodium bicarbonate solution extracted with ether and reduced in bulk. After recrystallisation from ethanol and water ethyl 5-chloro-3-p-chlorophenyl-1-phenyl-pyrazole-4-acetate is obtained with a 69% yield; F 51.5°–52.5°(from ether/petroleum ether).

In a similar manner with the corresponding alcohols the following esters are produced;

methyl 5-chloro-3-p-chlorophenyl-1-phenyl-pyrazole-4-acetate (F 66°–67.5°)

n-butyl 5-chloro-3-p-chlorophenyl-1-phenyl-pyrazole-4-acetate (Kp. $_{0.0001}$ 210–215°)

n-hexyl 5-chloro-3-p-chlorophenyl-1-phenyl-pyrazole-4-acetate.

EXAMPLE 20

Ethyl 5-chloro-3-p-chlorophenyl-1-phenyl-pyrazole-4-acetate 6.9 g of 5-chloro-3-p-chlorophenyl-1-phenyl-pyrazole-4-acetic acid, 70 ml of ethanol and 4 g of concentrated sulfuric acid are heated at boiling for 8 hours. The liquid is reduced in volume, poured into water and ice, extracted with ether, washed with sodium carbonate solution, the organic solution is dried and reduced in volume. Ethyl 5-chloro-3-p-chlorophenyl-1-phenyl-pyrazole-4-acetate is obtained with a yield of 85%; F 51.5°–52.5°.

EXAMPLE 21

5-Chloro-3-p-chlorophenyl-1-phenyl-pyrazole-4-acetamide 5g of 5-chloro-3-p-chlorophenyl-1-phenyl-pyrazole-4-acetonitrile and 10 ml of 96% sulfuric acid are stirred for 4 hours at room temperature. The batch is added to 50 g of ice, the precipitate is separated by vacuum filtering and washed with water. 5-Chloro-3-p-chlorophenyl-1-phenylpyrazole-4-acetamide is obtained with a 99% yield; F 192°–193°.

EXAMPLE 22

5-Chloro-3-p-chlorophenyl-1-phenyl-pyrazole-4-acetanilide a. 1.1 g of 5-chloro-3-p-chlorophenyl-1-phenyl-pyrazole-4-acetic acid, 15 ml of benzene and 0.5 g of phosphorus oxytrichloride are heated for 2 hours at boiling and 5-chloro-3-p-chlorophenyl-1-phenyl-pyrazole-4-acetyl chloride is obtained.

b. To the solution of the acid chloride in benzene 0.31 ml of aniline is added dropwise and stirring is carried out for 1 hour at room temperature. Filtration is carried out followed by recrystallisation. 5-Chloro-3-p-chlorophenyl-1-phenyl-pyrazole-4-acetanilide is obtained. F 201°–202°.

In a similar manner from 5-chloro-3-p-chlorophenyl-1-phenylpyrazole-4-acetyl chloride and ammonia morpholine, piperidine, ethylamine, 2-aminoethanol and phenylhydrazine the following pyrazole-4-acetic acid derivatives are obtained:

5-chloro-3-p-chlorophenyl-1-phenyl-pyrazole-4-acetamide F 192°–195°
5-chloro-3-p-chlorophenyl-1-phenyl-pyrazole-4-acetmorpholide F 182°–183°
5-chloro-3-p-chlorophenyl-1-phenyl-pyrazole-4-acetpiperidide
5-chloro-3-p-chlorophenyl-1-phenyl-pyrazole-4-acetic acid ethylamide
5-chloro-3-p-chlorophenyl-1-phenyl-pyrazole-4-acetic acid (2-hydroxyethyl)-amide
5-chloro-3-p-chlorophenyl-1-phenyl-pyrazole-4-acetic acid 2'-phenyl-hydrazide

EXAMPLE 23

5-Chloro-3-p-chlorophenyl-1phenyl-pyrazole-4-thioacetmorpholide 1.5 g of 5-chloro-3-p-chlorophenyl-1-phenyl-pyrazole-4-acetmorpholide, 8 ml of pyridine and 0.8 g of phosphorus pentasulfide are heated for 5 hours under reflux. Then 30 g of ice are added to the solution and the precipitate is vacuum filtered. 5-Chloro-3-p-chlorophenyl-1-phenyl-pyrazole-4-thioacetmorpholide is obtained; F 204°–205.5° (from dimethylformamide/H$_2$O).

EXAMPLE 24

5-Chloro-3-p-chlorophenyl-1-phenyl-pyrazole-4-acetamidoxime

To a hot solution of 1.0 g of 5-chloro-3-p-chlorophenyl1-phenyl-pyrazole-4-acetonitrile in 75 ml of ethanol a solution of 0.42 g of hydroxylamine hydrochloride in 6.05 ml of 1 N sodium bicarbonate solution is added and heating is carried out at boiling for 11 hours under reflux. The solution is evaporated to dryness and recrystallised from methanol/water. 5-Chloro-3-p-chlorophenyl-1-phenyl-pyrazole-4-acetamidoxime is obtained with a yield of 86%; F 184°–186° (from toluene).

EXAMPLE 25

10,000 tablets are produced with an active substance content of 50 mg from the following components:

| | |
|---|---|
| 500 g | 5-chloro-3-p-chlorophenyl-1-phenyl-pyrazole-4-acetic acid |
| 700 g | maize starch |
| 450 g | lactose |
| 30 g | amorphous silicic acid |
| 40 g | sodium lauryl sulfate |
| 50 g | polyvinylpyrrolidone |
| 160 g | pectin |
| 50 g | talc |
| 20 g | magnesium stearate |
| 2,000 g | |

The drug constituent, the maize starch, the lactose, the amorphous, silicic acid and the sodium lauryl sulfate are mixed and sieved. This mixture is moistened with a solution of the polyvinylpyrrolidone in 320 ml of alcohol and granulated through a sieve with a mesh width of 1.25 mm. The granules are dried at 40° and mixed with pectin, talc and magnesium stearate. The mixture is pressed to 200 mg tablets with a diameter of 8 mm.

EXAMPLE 26

10,000 capsules with a drug constituent content of 50 mg are prepared from the following components:

| | |
|---|---|
| 500 g | 5-chloro-3-p-chlorophenyl-1-phenyl-pyrazole-4-acetic acid |
| 495 g | microcrystalline cellulose |
| 5 g | amorphous silicic acid |
| 1,000 g | |

The drug constituent in a finely powdered form, the microcrystalline cellulose and the unpressed amorphous silicic acid are thorougly mixed and filled off in hard gelatin capsules, size 4.

EXAMPLE 27

100,000 tablets are produced with a content of a compound of this invention of 100 mg from the following components:
10.000 kg 5-chloro-3-p-chlorophenyl-1-phenyl-pyrazole-4-acetic acid
4.500 kg dextropropoxyphene hydrochloride
5.300 kg potato starch
0.500 kg polyvinylpyrrolidone (means molecular weight of 25.000)
1.800 kg: carboxymethyl cellulose
0.200 kg: magnesium stearate
5 l water The drug constituent of this invention, the dextropropoxyphene hydrochloride and the potato starch are sprayed in a fluid bed granulator with a solution of the polyvinylpyrrolidone in 5 l of water. The granules are dried to up to a relative humidity of 50 – 60 %, then the carboxymethyl cellulose and the magnesium stearate are added and the mixture is homogenized. After sieving the granulate is pressed to 170 mg tablets with a diameter of 8 mm.

EXAMPLE 28

1,000 suppositories are produced with a drug constituent content of 100 mg from the following components:
0.106 kg 5-chloro-3-p-chlorophenyl-1-phenyl-pyrazole4-acetic acid, sodium salt
2.393 kg suppocire BM The suppocire BM is heated up to 40° – 50° C. The sodium salt is stirred into this melt. The batch is homogenized and poured into molds.

EXAMPLE 29

A gel with a drug constituent content of 1% is prepared from the following components:
1.00 kg 5-chloro-3-p-chlorophenyl-1-phenyl-pyrazole-4-acetic acid
1.50 kg Carbopol 934
0.30 kg Cremophor EL
~0.40 kg sodium hydroxide solution
20.00 kg propylene glyocol
ad 100.00 kg water The Carbopol 934 is suspended in the water under vigorous stirring. The mixture is left for 1 hour, then the drug constituent, the Cremophor EL and the propylene glycol are added, followed by slow addition of the sodium hydroxide solution under agitation until a pH of 8 is reached.

EXAMPLE 30

A suspension with a drug constituent content of 50 mg per 5 ml is produced from the following components:
1.00 kg 5-chloro-3-p-chlorophenyl-1-phenylpyrazole-4-acetic acid
2.70 kg Tylose C30
0.11 kg sodium cyclamate 0.08 kg sorbic acid
ad 100 l water The Tylose C 30 is put into 90 l of water under vigorous stirring; the drug constituent of this invention,, the cyclamate and the sorbic acid are added, the volume is completed up to 100 l. The mixture is passed through a corundum disk crusher, vented and filled up into 5 ml fractions.

EXAMPLE 31

A batch for 100 l of an injection solution is produced from the following components:
4.152 kg 5-chloro-3-p-chlorophenyl-1-phenyl-pyrazole-4-acetic acid, sodium salt
0.150 kg prednisolone
0.200 kg sodium disulfite
0.025 kg cysteine hydrochloride
26.000 kg 1,2-propylene glycol
ad 100 l water 65 l of distilled water are heated up to 80° C bubbling nitrogen through the fluid, the drug constituent of this invention and the prednisolone are added. After complete dissolution of the added compounds the solution is cooled down to room temperature. The sodium disulfite, the cysteine hydrochloride and the propylene glycol are added, the volume is completed up to 100 l and the mixture is agitated for complete dissolution.

EXAMPLE 32

A bath for 100 l of an injection solution is produced in analogy to the procedure described in example 31 but replacing 0.150 kg prednisolone with 0.080 kg dexamethasone.

Following the procedure described in examples 27 to 32 pharmaceutical compositions containing 5-chloro-1,3-diphenylpyrazole-4-acetic acid and -4-sodium acetate, respectively, are produced replacing 5-chloro-3-p-chlorophenyl-1-phenylpyrazole-4-acetic acid and -4-sodium acetate, respectively, with the corresponding 5-chloro-1,3-diphenyl-pyrazole derivative in the same amount.

What is claimed is:

1. A pharmaceutically-acceptable member selected from the group consisting of a 1,3-diaryl-5-halopyrazole-4-acetic acid and a salt thereof; the 5-halo being 5-fluoro, 5-chloro or 5-bromo, and each aryl being, independently, a) phenyl or b) phenyl substituted by a substituent selected from the group consisting of halo, p-(lower)alkoxy and p-(lower)alkyl.

2. A pyrazole-4-acetic acid derivative which is a pharmaceutically-acceptable member selected from the group consisting of 5-halo-1-phenyl-3-(substituted or unsubstituted phenyl)pyrazole-4-acetic acid and a salt thereof; substituted phenyl being halophenyl, p-(lower alkoxy)phenyl or p-(lower alkyl)phenyl, and each halo being bromo or chloro.

3. A pyrazole-4-acetic acid derivative according to claim 2 wherein substituted phenyl is p-chlorophenyl, p-methoxyphenyl or p-isobutylphenyl.

4. A pyrazole-4-acetic acid derivative according to claim 1 wherein the aryl in the 1-position is phenyl; the aryl in the 3-position is a member selected from the group consisting of phenyl, p-chlorophenyl and p-bromophenyl; and halo is fluoro or chloro.

5. A pyrazole-4-acetic acid derivative of formula I*

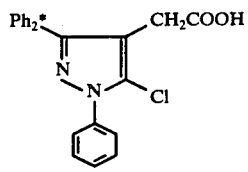

in which
Ph$_2$* is a unsubstituted phenyl or p-chlorophenyl or a pharmaceutically acceptable salt thereof.

6. 5-Chloro-1,3-diphenyl-pyrazole-4-acetic acid or a pharmaceutically acceptable salt thereof.

7. 5-Chloro-3-p-chlorophenyl-1-phenyl-pyrazole-4-acetic acid or a pharmaceutically acceptable salt thereof.

8. 5-Chloro-3-p-methoxyphenyl-1-phenyl-pyrazole-4-acetic acid or a pharmaceutically acceptable salt thereof.

9. 5-Chloro-3-p-isobutylphenyl-1-phenyl-pyrazole-4-acetic acid or a pharmaceutically acceptable salt thereof.

10. 5-Bromo-1,3-diphenyl-pyrazole-4-acetic acid or a pharmaceutically acceptable salt thereof.

11. A pharmaceutically-acceptable composition useful for the treatment of inflammation, pain or fever and having from 1 to 95 percent by weight of at least one pharmaceutically-acceptable member according to claim 10 and pharmaceutical vehicle or diluent.

12. A composition according to claim 11 wherein the pharmaceutically-acceptable member is 5-chloro-3-p-chlorophenyl-1-phenylpyrazole-4-acetic acid.

13. A composition according to claim 11 which contains from 10 to 85 percent by weight of at least one pharmaceutically-acceptable member.

14. A composition according to claim 11 in tablet, dragee, granule, capsule, sirup, solution, suspension, ointment, or suppository form.

15. A composition according to claim 14 in the form of a potable solution or suspension.

16. A composition according to claim 14 in sterile solution form.

17. A composition according to claim 14 in isotonic solution form.

18. A therapeutic method for treating a mammal suffering fron one or more systems of inflammation, pain or fever which comprises administering to the mammal a sympton-reducing-effective, pharmacologically-compatible dose of composition according to claim 11.

* * * * *

UNITED STATES PATENT AND TRADEMARK OFFICE
CERTIFICATE OF CORRECTION

PATENT NO. : 4,042,702
DATED : August 16, 1977
INVENTOR(S) : RAINER

It is certified that error appears in the above-identified patent and that said Letters Patent are hereby corrected as shown below:

Title page, item [56], line 7, "Intersciecne" should read --Interscience--. Column 1, line 28, "denote respectively" should read --denote, respectively,--; line 43, "denote" should read --denote,--; line 45, "or" should read --or,--; "atom" should read --atom,--. Column 2, about line 5, to the right of the formula insert --I,--; line 26, "radical and," should read --radical,--; line 56, "new" should read --now--. Column 4, line 27, "hydroxymimino" should read --hydroxyimino--; line 39, "radica" should read --radical--; line 44, "1" should read --10--; line 61, "bodimment" should read --bodiment--; line 62, "amines" should read --amides--; line 67, "formulae" should read --formula--. Column 5, line 3, "and" should read --and,--; line 9, "nitric" should read --nitric acid--; line 20, "esters" should read --esters,--; line 26, "imideacid" should read --imide acid--. Column 6, line 19, "-4    -thi-" should read -- -4-thi- --; line 49, "also" should read --also on--. Column 8, line 44, "slitting" should read --splitting--; line 46, "esters" should read --esters,--; line 52, "dialkylamines" should read --dialkylamines,--; line 55, "-N-" should read --N- --. Column 9, line 60, "(ED$_{25}$]" should read --[ED$_{25}$]--. Column 10, lines 1 through 20, "was determined ... manner" should read
--was determined on the retarding inflammation at the carrageenin edema of the rear paw of the rat [Winter et al., Proc. Soc. exp. Biol. Med., 111 (1962) 544], wherein in Table 2 those doses are shown which cause a mean retardation

UNITED STATES PATENT AND TRADEMARK OFFICE
CERTIFICATE OF CORRECTION

PATENT NO. : 4,042,702
DATED : August 16, 1977
INVENTOR(S) : Rainer

It is certified that error appears in the above-identified patent and that said Letters Patent are hereby corrected as shown below:

of 25% 3 and 5 hours after single administration of the substance to be tested;

on the retardation at the ultraviolet erythema of the skin on the back of the guinea pig [Winder et al., Arch. int. Pharmacodyn., 116 (1958) 261], wherein in table 1 those doses are shown which cause a retardation of 25% 5 hours after irradiation;

on a chronic inflammation model (cotton granuloma) wherein the influence of the compounds on the granulation tissue formation after subcutaneous implantation of cotton plugs in rats was studied after daily administration on 7 following days in taking pattern from the method described by Winter et al. [J. Pharmacol. exp. Therap., 141 (1963) 369], in table 1 those doses are shown which inhibit the reformation of the granulation tissue by 20% ($ED_{20}$).

The lethal doses were determined in usual manner.--. Column 11, line 29, "example" should read --example,--. Column 12, line 15, "traganth" should read --tragacanth--; line 35, "traganth" should read --tragacanth--; line 57, "pyridizine" should read --pyridazine--. Column 13, line 13, "which" should read --which,--; line 14, "solution" should read --solution,--; line 39, "isotutylphenyl-" should read --isobutylphenyl- --; line 47, "acetonitrile the following compounds" should read --acetonitrile
the following compounds--; line 62, "acid are obtained in a similar manner" should read

UNITED STATES PATENT AND TRADEMARK OFFICE
CERTIFICATE OF CORRECTION

PATENT NO. : 4,042,702

DATED : August 16, 1977

INVENTOR(S) : Rainer

It is certified that error appears in the above-identified patent and that said Letters Patent are hereby corrected as shown below:

--acid
are obtained in a similar manner. Column 14, line 24, "thioacetic ... hydrolysis" should read --thioacetate
using alkaline hydrolysis--; lines 26 through 46, "acid (F 179.5°-181°). ... acid (F 179.5°-181°)." should read --acid (F 179.5° -181°).--; lines 51 and 52, "methyl ... hydrolysis" should read --methyl 5-bromo-1,3-diphenyl-pyrazole-4-acetate
  by alkaline hydrolysis--.

Column 15, line 11, "example 2.5-Chloro-" should read --example 2. 5-Chloro- --; line 17, "chlorphenyl" should read --chlorophenyl--; lines 35 and 36, "acetamidine-hydrochloride ... acid" should read --acetamidine-hydrochloride
   by hydrolysis with sulfuric acid--; line 53, "acetimideethyl" should read --acetimide-ethyl--; lines 59 and 60, "pyrazolyl) ... acid" should read --pyrazolyl)-methyl]-imidazoline
by hydrolysis with hydrochloric acid--. Column 16, line 14, "3.5 3-p-" should read --3.5 g of 5-chloro-3-p- --; line 45, "144°-145°" should read --144°-145.5°--; line 54, "pyrazole" should read --pyrazoline--; line 66, "5 to 10°" should read --5° to 10°--. Column 17, line 8, "169°" should read --169.5°--; line 12, "10°" should read --110°--; line 16 should begin at the margin; line 21, "boxaldehyde are prepared." should read --boxaldehyde
are prepared.--; line 22, "3-p-chloro-phenyl-" should read --3-p-chlorophenyl- --; line 42, "2pyrazoline" should read --2-pyrazoline--;

UNITED STATES PATENT AND TRADEMARK OFFICE
CERTIFICATE OF CORRECTION

PATENT NO. : 4,042,702                                   Page 4 of 5

DATED      : August 16, 1977

INVENTOR(S) : Rainer

It is certified that error appears in the above-identified patent and that said Letters Patent are hereby corrected as shown below:

line 45, "-carboxaldehyde 175" should read -- -carboxaldehyde--; line 46, "g" should read --175 g--; line 54, "2 n" should read --2 N--; line 58, "85" should read --85%--. Column 18, line 14, "3p" should read --3-p--; line 36, "140.4°" should read --140.5°--; line 60, "9.6°" should read --96.5°--. Column 19, line 24 [26], "3p" should read --3-p--; line 38, "deter-" should read --ter- --; line 39, "mined." should read --minated.--. Column 20, line 20, "210-215°" should read --210°-215°--; line 65, "ammonia" should read --ammonia,--. Column 21, line 15, "1phenyl" should read --1-phenyl--; line 30, "phenyl1" should read --phenyl-1--; line 54, "amorphous," should read --amorphous--. Column 22, line 19, "(means" should read --(mean--; line 20, "25.000" should read --25,000--; line 21, "kg:" should read --kg--; line 22, "kg:" should read --kg--; line 31, "ing" should read --ing,--; line 38, "pyrazole4-" should read --pyrazole-4- --; line 29 [39], "kg ... BM" should read --kg Suppocire® BM--; line 40, "suppocire BM" should read --Suppocire® BM--; line 49, "Carbopol" should read --Carbopol®--; line 50, "Cremophor" should read --Cremophor®--; line 54, "Carbopol" should read --Carbopol®--; line 67, Tylose" should read --Tylose®--. Column 23, line 3, "Tylose" should read --Tyolose®--; line 32, "bath" should read --batch--.

UNITED STATES PATENT AND TRADEMARK OFFICE
CERTIFICATE OF CORRECTION

PATENT NO. : 4,042,702

DATED : August 16, 1977

INVENTOR(S) : Rainer

It is certified that error appears in the above-identified patent and that said Letters Patent are hereby corrected as shown below:

Column 24, lines 20-21, "$Ph_2$*" ... thereof." should read

--$Ph_2$* is an unsubstituted phenyl or p-chlorophenyl or a pharmaceutically-acceptable salt thereof.--; line 23, "pharmaceutically acceptable" should read --pharmaceutically-acceptable--; lines 25, 28, and 31, "pharmaceutically acceptable" (each occurrence) should read --pharmaceutically-acceptable--; line 34, "pharmaceutically acceptable" should read --pharmaceutically-acceptable--; line 39, "claim 10" should read --claim 1--; line 56, "fron" should read --from--; "systems" should read --symptoms--; line 58, "sympton" should read --symptom--.

Signed and Sealed this

Tenth Day of April 1979

[SEAL]

Attest:

RUTH C. MASON
Attesting Officer

DONALD W. BANNER
Commissioner of Patents and Trademarks